United States Patent
Meinicke et al.

(10) Patent No.: US 8,377,396 B2
(45) Date of Patent: Feb. 19, 2013

(54) GRIPPING TOOL, DOSAGE TOOL AND TOOL SUPPORT FOR AN AUTOMATIC LABORATORY MACHINE

(75) Inventors: Matthias Meinicke, Norderstedt (DE); Jens Wilmer, Ahrensburg (DE)

(73) Assignee: Eppendorf AG, Hamburg (DE)

( * ) Notice: Subject to any disclaimer, the term of this patent is extended or adjusted under 35 U.S.C. 154(b) by 70 days.

(21) Appl. No.: 12/329,950

(22) Filed: Dec. 8, 2008

(65) Prior Publication Data

US 2009/0087343 A1 Apr. 2, 2009

Related U.S. Application Data

(62) Division of application No. 10/673,071, filed on Sep. 26, 2003, now Pat. No. 7,462,327.

(30) Foreign Application Priority Data

Oct. 12, 2002 (DE) .................................. 102 47 731

(51) Int. Cl.
*B01L 3/00* (2006.01)
*B01L 99/00* (2006.01)
(52) U.S. Cl. ........ 422/546; 422/544; 422/500; 422/509; 422/511; 422/518; 422/63
(58) Field of Classification Search .................. 422/104, 422/63–68.1, 500, 509, 511, 518, 107, 544, 422/546
See application file for complete search history.

(56) References Cited

U.S. PATENT DOCUMENTS

| 4,579,380 A | * | 4/1986 | Zaremsky et al. ......... 294/119.1 |
| 4,598,942 A | * | 7/1986 | Shum et al. .................. 294/106 |
| 4,611,846 A | | 9/1986 | Feiber et al. |
| 4,680,523 A | * | 7/1987 | Goumas et al. ............... 318/685 |
| 4,699,414 A | * | 10/1987 | Jones .......................... 294/119.1 |
| 4,808,898 A | * | 2/1989 | Pearson .................... 318/568.21 |
| 4,955,653 A | * | 9/1990 | Beals ......................... 294/119.1 |
| 5,080,864 A | | 1/1992 | Shaw |
| 5,282,978 A | | 2/1994 | Polk et al. |
| 5,398,556 A | | 3/1995 | Lang |
| 5,439,649 A | | 8/1995 | Tseung et al. |
| 5,455,006 A | | 10/1995 | Aota et al. |
| 5,479,969 A | | 1/1996 | Hardie et al. |
| 5,497,670 A | | 3/1996 | Carl |
| 5,538,305 A | * | 7/1996 | Conway et al. ............ 294/119.1 |
| 5,540,890 A | | 7/1996 | Clark et al. |
| 5,551,828 A | | 9/1996 | Iles |
| 5,599,500 A | | 2/1997 | Jones |
| 5,609,381 A | * | 3/1997 | Thom et al. ................. 294/119.1 |
| 5,612,227 A | | 3/1997 | Inoue et al. |

(Continued)

FOREIGN PATENT DOCUMENTS

| DE | OS 2 326 244 | 12/1974 |
| DE | 31 24 948 | 3/1982 |

(Continued)

*Primary Examiner* — Brian R Gordon
(74) *Attorney, Agent, or Firm* — Vidas, Arrett & Steinkraus, P.A.

(57) ABSTRACT

Gripping tool for automatic laboratory machines, with gripping appliances for gripping vessels, an appliance for converting and/or transferring of movements, the power take-off of which is coupled with the gripping appliances in order to drive them, a coupling appliance for detachable connection with a drive appliance of a tool support of an automatic laboratory machine, which is coupled with the drive of the appliance for converting and/or transferring in order to drive it, and a mounting appliance for detachable mounting of the gripping tool on the tool support of the automatic laboratory machine, while the coupling appliance is connected with the drive appliance of the tool support.

4 Claims, 8 Drawing Sheets

U.S. PATENT DOCUMENTS

Figure 1:
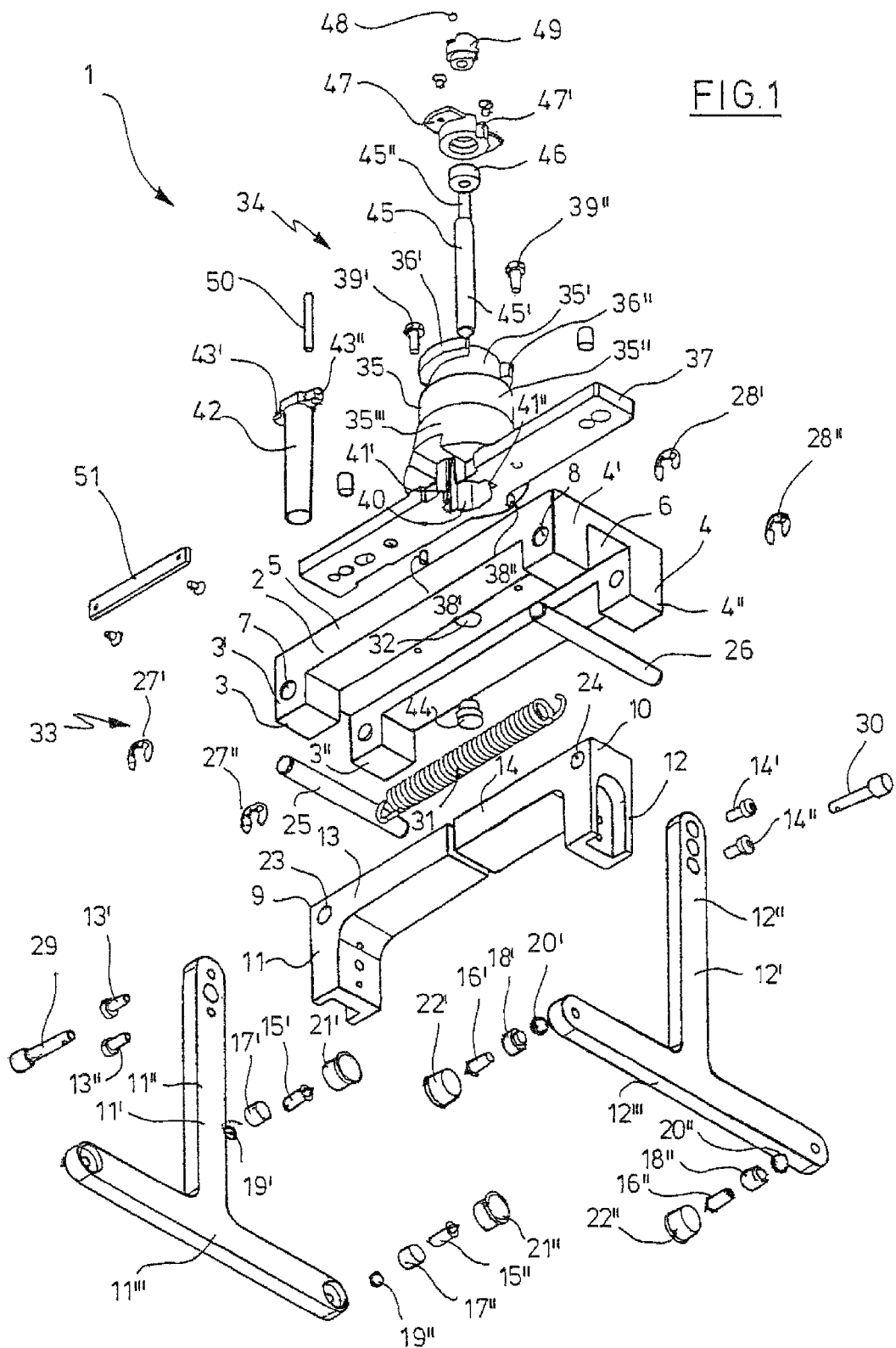

| | | |
|---|---|---|
| 5,873,394 A | 2/1999 | Meltzer |
| 5,906,795 A | 5/1999 | Nakashima et al. |
| 6,159,199 A | 12/2000 | Syska et al. |
| 6,203,760 B1 | 3/2001 | van der Plaats et al. |
| 6,423,548 B1 | 7/2002 | Newberg et al. |
| 6,458,324 B1 | 10/2002 | Schinzel |
| 6,540,964 B2 * | 4/2003 | Kohrmann et al. ............ 422/100 |
| 6,544,799 B1 | 4/2003 | Lewis et al. |
| 6,588,464 B2 | 7/2003 | Scatizzi |
| 6,589,789 B1 | 7/2003 | Hubert et al. |
| 6,652,015 B1 | 11/2003 | Carney et al. |
| 6,669,432 B2 | 12/2003 | Hamel et al. |
| 6,818,182 B2 | 11/2004 | Le Comte et al. |
| 6,843,357 B2 | 1/2005 | Bybee et al. |
| 6,846,680 B2 | 1/2005 | Friswell et al. |
| 6,883,958 B2 | 4/2005 | Mayer |
| 6,887,428 B2 | 5/2005 | Wemz et al. |
| 7,128,874 B2 | 10/2006 | Kittock et al. |
| 7,141,213 B1 | 11/2006 | Pang et al. |
| 2002/0076351 A1 | 6/2002 | Wernz et al. |
| 2002/0102736 A1 | 8/2002 | Kittock et al. |
| 2003/0223916 A1 | 12/2003 | Testrut et al. |

FOREIGN PATENT DOCUMENTS

| | | |
|---|---|---|
| DE | 40 34 422 A1 | 8/1991 |
| DE | 44 12 286 | 10/1995 |
| DE | 198 01 178 | 5/1999 |
| DE | 693 23 851 | 7/1999 |
| EP | 0 226 867 A2 | 11/1986 |
| EP | 0 734 769 | 3/1996 |
| EP | 0 763 739 A1 | 3/1996 |
| EP | 1 291 658 A1 | 7/2001 |

* cited by examiner

GRIPPING TOOL, DOSAGE TOOL AND TOOL SUPPORT FOR AN AUTOMATIC LABORATORY MACHINE

CROSS-REFERENCE TO RELATED APPLICATIONS

This application is a Divisional application from Ser. No. 10/673,071, the contents of which is hereby incorporated by reference

STATEMENT REGARDING FEDERALLY SPONSORED RESEARCH

Not applicable.

BACKGROUND OF THE INVENTION

Automatic laboratory machines serve for the automatic processing of mostly liquid samples in the laboratory. In particular, tempering, mixing, filtration, chemical reaction and dosage of the samples belong to the processings. During or between the processings, respectively, the samples are stored in vessels, in particular in laboratory vessels, vessel chains, microtiter plates, filter plates and other plates with a plurality of sample receivers. The vessels have to be moved or transported, respectively, between different positions of storage and processing, respectively. For this purpose, conventional automatic laboratory machines are equipped with an automatic gripping appliance, which enables gripping, transporting, moving and setting down of the vessels as well as covering of the vessels with special lids.

Further, conventional automatic laboratory machines have dosage appliances. Dosage appliances are already known which comprise a tool support and a dosage tool, detachably connectable with it, which has at least one piston-cylinder unit. By moving the piston into opposite directions, sample liquid is aspired or set free, respectively, through a dosage opening. In direct displacement systems, the piston has contact to the liquid, and in insulating air cushion systems, an insulating air cushion exists between the piston and the liquid. Often the liquid is received in replaceable pipette systems, which have a dosage opening at the bottom and a pinning up opening for detachable connection with the dosage tool on the topside. By exchanging the dosage tool, it is possible to perform different dosage tasks. The tool support is movable between different positions, in order to accept or to release, respectively, dosage tools, pipette points or samples, respectively.

Departing from this, the invention is based on the objective to provide a simplified gripping and dosage technique for automatic laboratory machines.

BACKGROUND SUMMARY OF THE INVENTION

The inventive gripping tool for automatic laboratory machines has gripping appliances for gripping vessels, an appliance for converting and/or transferring of movements, the power take-off of which is coupled with the gripping appliances in order to drive them, a coupling appliance for detachable connection with a drive appliance of a tool support of an automatic laboratory machine, which is coupled with the drive of the appliance for converting and/or transferring in order to drive it, and a mounting appliance for detachable mounting of the gripping tool on the tool support of the automatic laboratory machine, while the coupling appliance is connected with the drive appliance of the tool support.

Conventional tool supports of automatic laboratory machines are applicable with inventive gripping tools for the manipulation of laboratory vessels, lids of vessels and other objects. Different gripping tools for variable gripping tasks can be mounted on one tool support. Furthermore, it is possible to equip the same tool support with different dosage tools, in order to use it for dosage purposes. In doing so, the drive appliance of the tool support is usable for the operation of different gripping appliances, as well as for the operation of different dosage appliances. A displacement appliance for displacing the tool support along and/or for at least one spatial axis is usable for the displacement of the gripping tool as well as for the displacement of the dosage tool. It can be resorted to conventional tool supports, which are already equipped with corresponding drive appliances. Thus, the inventive gripping appliances make considerable cost savings possible, because they do not need any own drive appliances, but co-operate with a commonly applicable tool support.

The gripping appliances can be realized in different ways. For instance, with the gripping appliances it can be dealt with arms which can be parallel drawn together or apart, respectively. According to a form of realization, the gripping appliances are swingably mounted gripping levers. These can be swingable together or apart, respectively, around parallel axis. According to a form of realization, the grapplers are replaceable, in order to adapt the gripping tool to different purposes of usage.

According to a form of realization, the gripping levers have approximately parallel grapplers and offset driving arms directed towards each other, with the adjacent ends of which the power take-off of the appliance for converting and/or transferring is coupled. This enables a simple transfer of the movement of the power take-off to the gripping appliances. The grapplers are swung together or apart, respectively, through actuation of the driving arms.

For secure grasping of vessels, according to one form of realization the gripping appliances have needles directed towards each other and/or liners for pricking into walls and/or grasping on the surface structures of the walls of vessels. By pricking the needles into vessels made of plastic material (polycarbonate or polypropylene, for instance), it is possible to grasp them securely. The vessels or other objects are grasped securely by frictional connection, and an undesired exertion of force, e.g. upon a seal of a vacuum chamber, is avoided. For instance, the liners can engage in recesses of the vessel walls, lap over projections on the vessel walls or grasp the vessels at other surface shapings.

According to a form of realization, the gripping appliances have protective sleeves with springs, disposed concentrically around the needles, and/or liners disposed concentrically around the needles. The protective sleeves spring back upon pricking the needles into the wall of a vessel. They can prevent injuries of the operating personnel upon a manual intervention (e.g. when eliminating troubles or inserting or taking out a vessel from the run). A similar function is performed by the liners, which preferably stand somewhat back with respect to the needles, so that the needles and the liners are simultaneously usable for the grasping of the vessels.

According to a form of realization, a spring appliance clamping the gripping appliances together exists. Through this spring appliance, the gripping appliances are always pre-stressed, and consequently always in the gripping position. Through this, the gripping appliances are kept on the vessels with a defined tension. The vessels can therefore be securely kept even at current break or at emergency disconnection. On the other hand, it is possible in such a situation to open the gripping appliances manually, in order to remove a vessel.

According to a form of realization, the spring appliance presses the gripping appliances against the power take-off of the appliance for converting and/or transferring, whereby a permanent coupling of the gripping appliance with the power take-off is secured on the one hand, its release is made possible on the other hand for the case of a manual removal of the vessel.

The appliance for converting and/or transferring of movements can be solely an appliance for transferring movements, which a linear or rotatory drive motion transfers onto the gripping appliance. According to a form of realization, the appliance for converting and/or transferring has an axially movable, threaded nut secured against rotation, acting on the gripping appliances with one front side, and a spindle, screwable in the threaded nut, connected with the coupling appliance in a manner secured against rotation. This appliance for converting and/or transferring transforms a rotatory movement into an axial movement, in order to transfer it onto gripping appliances realized as gripping levers, for instance.

According to a form of realization, the gripping tool has an appliance for indicating the position of the gripping appliances, which is feelable by a sensor of the tool support when the gripping tool is mounted on the tool support. In this occasion, the tool support can determine the respective positions of the gripping appliances, in order to control their movements accurately. For instance, this can serve for a determination of the adjustment of the gripping appliances after accommodation of a gripping tool by the tool support. But this can also be used for a permanent detection of the respective position of the gripping appliances on their actuation, in order to realize the gripping movements as accurately as possible.

According to a form of realization, the appliance for indicating is a pin, fixedly connected with the threaded nut. Upon alignment of the pin parallel to the thread axis, the respective axial position of the threaded nut can be determined by feeling the pin. From this, the position of the gripping appliances coupled with the threaded nut can be determined.

According to a form of realization, the coupling appliance is a driving feature, connected with the drive of the appliance for converting and/or transferring in a manner secured against rotation, with at least one working surface for a rotational drive appliance. With the working surface, it can be dealt with the side walls of an axially and radially oriented groove, into which the rotational drive appliance engages with a correspondingly formed spring.

According to a form of realization, the mounting appliance has a hollow mounting spigot, and the coupling appliance is disposed in the mounting spigot or sticks out of it, and/or the indicating appliance is disposed in the mounting spigot or sticks out of it. Through this, the synchronous fixation and coupling of the gripping tool on the tool support and with its drive appliance, and/or the association of the indicating appliance with a sensor of the tool support is promoted. According to a form of realization, the mounting spigot has at least one cylinder part and at least one conical base part, which is advantageous for the insertion and centering of the mounting spigot in an accommodation. The cylinder part is situated on the free end of the mounting spigot, by which the latter is inserted into an accommodation. At the end of the insertion duct, the base part fits closely to a corresponding cone of the accommodation, and through this the centering is effected.

In principle, the mounting spigot can be connected non-positively fitting with the tool support, which can have a clamping appliance for clamping in the mounting spigot, for instance. According to a form of realization, the mounting spigot on the outside has a connection part with a detachable positively fitting connection, which can co-operate with a further positively fitting connection part of the tool support. According to a form of realization, the connection part is a bayonet-type connection part, to which a complementary bayonet-type connection part of a tool support has to be associated.

The inventive dosage tool for automatic laboratory machines has at least one piston-cylinder appliance, an appliance for converting and/or transferring of movements, the power take-off of which is coupled with the piston-cylinder appliance in order to drive it, a coupling appliance for detachable connection with a drive appliance of a tool support of an automatic laboratory machine, which is coupled with the drive of the appliance for converting and/or transferring in order to drive it, a mounting appliance for detachable mounting of the dosage tool on the tool support of the automatic laboratory machine, while the coupling appliance is connected with the drive appliance of the tool support, an appliance for indicating the position of the piston of the piston-cylinder appliance, which is feelable by a sensor of the tool support while the dosage tool on the tool support is mounted.

By the reason that the inventive dosage tool has an appliance for indicating the position of the piston, it is possible via a sensor of the tool support, to determine the position of the piston accurately and to control the dosage accurately via the drive appliance. This can be used for an initial determination of the position of the piston after the mounting of the dosage tool on the tool support, and for a continuous surveillance of the position of the piston when dosing.

The appliance for converting and/or transferring can also be realized in different ways, depending on whether which movement the drive appliance generates. If the drive appliance generates a linear movement, an appliance for transferring the linear movement to a piston is sufficient. A drive appliance which generates a rotational movement has, according to one form of realization, the appliance for converting and/or transferring and an axially movable, threaded nut secured against rotation, acting on the piston of the piston-cylinder appliance with one front side, and a spindle, screwable in the threaded nut and connected with the coupling appliance in a manner secured against rotation. This and the following forms of realization of the dosage tools correspond to forms of realization of the gripping tool already clarified above, which are useful with respect to the advantageous coupling with the same tool support.

Thus, according to a form of realization, the appliance for indicating is a pin, fixedly connected with the threaded nut. According to a form of realization, the coupling appliance is a driving feature, connected with the drive of the appliance for converting and/or transferring in a manner secured against rotation, with at least one working surface for a rotational drive appliance. According to a form of realization, the mounting appliance has a hollow mounting spigot, and the coupling appliance is disposed in the mounting spigot or sticks out of it, and/or the indicating appliance is disposed in the mounting spigot or sticks out of it. According to a form of realization, the mounting spigot has at least one cylinder part and at least one conical base part. According to a form of realization, the mounting spigot has a connection part of a detachable positively fitting connection on the outside. This is a bayonet-type connection part, according to a form of realization. Insofar, the further advantages of the corresponding forms of realization of the gripping tool, already mentioned above, do apply.

According to a form of realization, which also applies for the gripping tool as well as for the dosage tool, a chip is attached on the respective tool, which contains data of the respective tool, which are readable from the outside. Through this, it is possible to read the data of the respective tool from the outside, for instance when it is placed in the tool support, in order to take the data of the tool into account when it is used.

The inventive tool support for an automatic laboratory machine, which is particularly suited for holding and moving of gripping tools and dosage tools of the type mentioned above, has a drive appliance for driving of a gripping tool or of a dosage tool at option, a further coupling appliance for connecting the drive appliance with a coupling appliance of a gripping tool or of a dosage tool at option, a further mounting appliance for mounting the mounting appliance of a gripping tool or of a dosage tool at option, while the coupling appliances of the tool support and the gripping tool or the dosage tool are coupled with each other, and a control appliance for controlling the movements of the gripping tool or of a dosage tool at option.

Through the fact that the inventive tool support has a control appliance which controls the movement of the gripping tool or of a dosage tool at option, it is possible to control the movement of a gripping tool as well as of a dosage tool with the same tool support, which these have to perform in an automatic laboratory machine. Thus, a gripping tool can be controlled such that it seizes and disengages a vessel, transports it, turns it, shakes it, stacks it or performs every other imaginable movement. With a dosage tool, particularly the taking up, taking off, diluting, dispensing, mixing and transferring of samples can be controlled.

Forms of realization of the tool support correspond to the forms of realization of the gripping tool and the dosage tool, already mentioned above.

Thus, according to a form of realization, the tool support is equipped with a rotational drive appliance.

According to a form of realization, the further coupling appliance has at least one further working surface for a rotational drive appliance.

According to a form of realization, the mounting appliance has an accommodation for a mounting spigot of a gripping- or dosage tool and the further coupling appliance is associated to the accommodation, in order to couple in the coupling appliance of the gripping- or dosage tool when the mounting spigot is disposed in the accommodation.

According to a form of realization, the accommodation has at least one cylindrical portion and at least one conical initial portion.

According to a form of realization, a further bayonet-type connection part for detachable connection with a bayonet-type connection part of the mounting spigot of a gripping- or dosage equipment is associated to the further accommodation.

According to a further form of realization, the further bayonet-type connection part can be driven by a motor, and the control appliance controls the movements of the further bayonet-type connection part. This makes possible an automatic connection of the tool support with a gripping- or dosage tool in an automatic laboratory machine.

According to a form of realization, a sensor is associated to the accommodation in order to feel an appliance for indicating of a gripping- or dosage tool, disposed in the accommodation with the mounting spigot, the sensor being connected with the control appliance, in order to control the movements, depending on the position of the gripping appliances or the piston.

According to a form of realization, the tool support has a further sensor for feeling a chip, containing data of a gripping- or dosage tool, which is connected to the control appliance, in order to control the movements, depending on the data of the gripping tool or of the dosage tool.

According to a form of realization, the tool support has a displacement facility for displacing the tool support along at least one and/or for at least one spatial axis, which displacement is controllable by the control appliance in order to reach and/or perform different vessel positions and/or movements of the gripping tool and the dosage tool with the gripping tool.

After all, the invention embraces a system for gripping of vessels and/or dosage of samples with a gripping tool of the aforementioned type, and/or a dosage tool of the aforementioned type, and a tool support of the aforementioned type.

BRIEF DESCRIPTION OF THE SEVERAL VIEWS OF THE INVENTION

Figure 2:
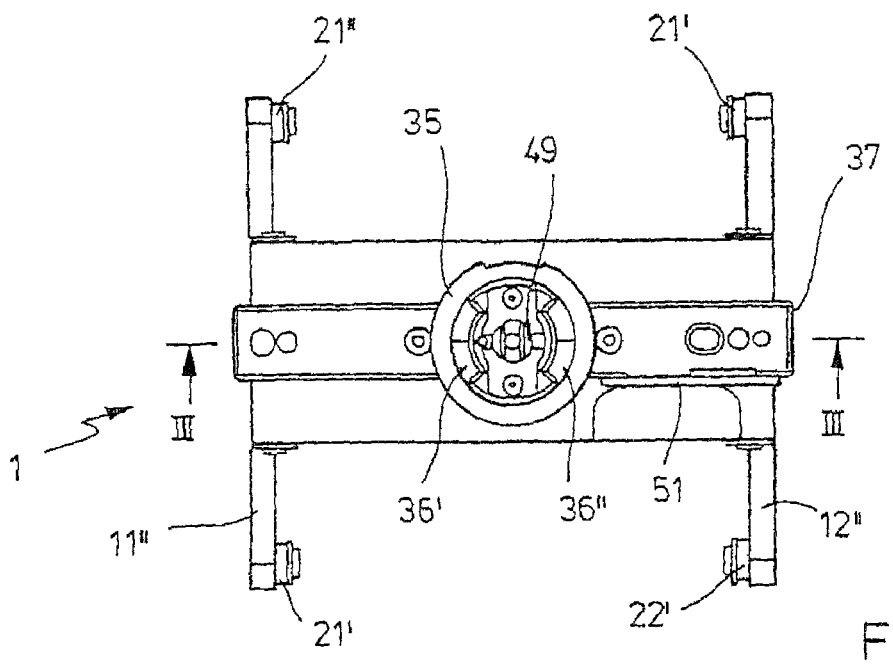
Figure 3:
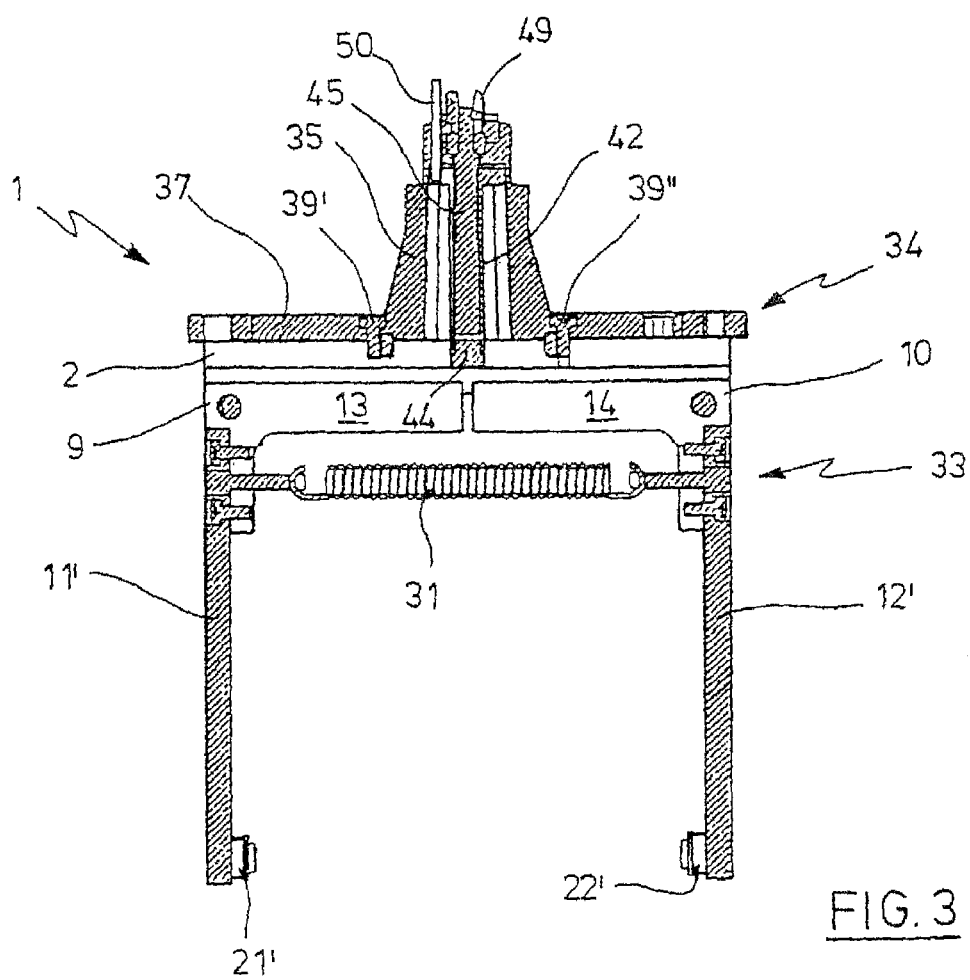
Figure 4:
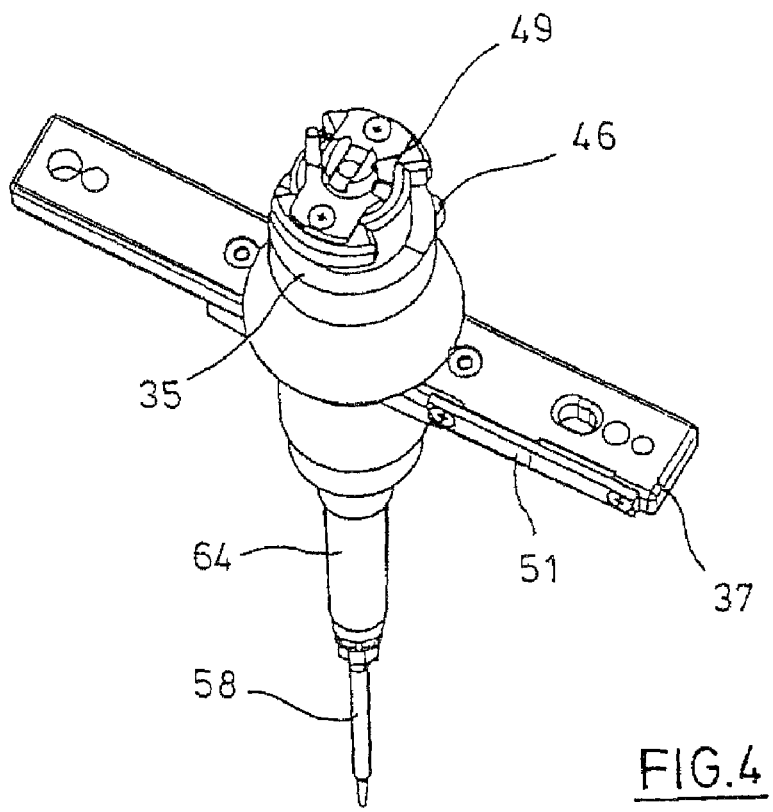
Figure 5:
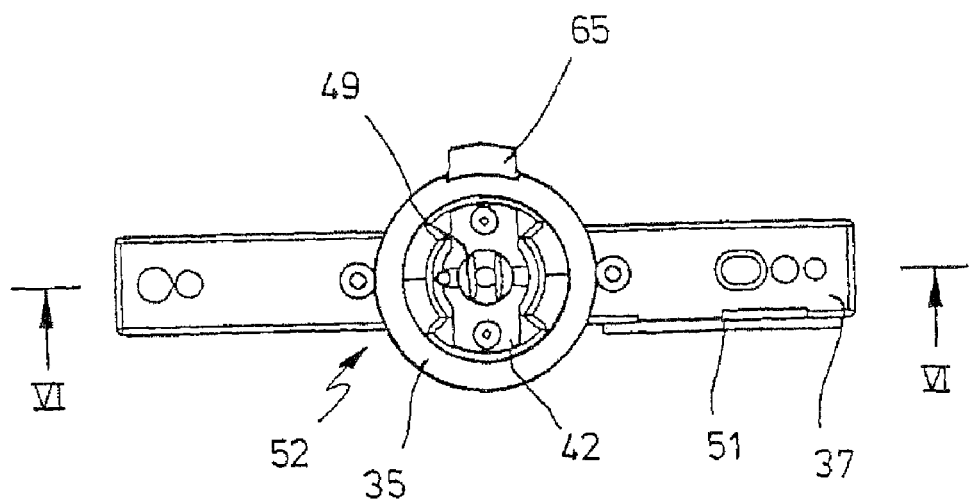
Figure 6:
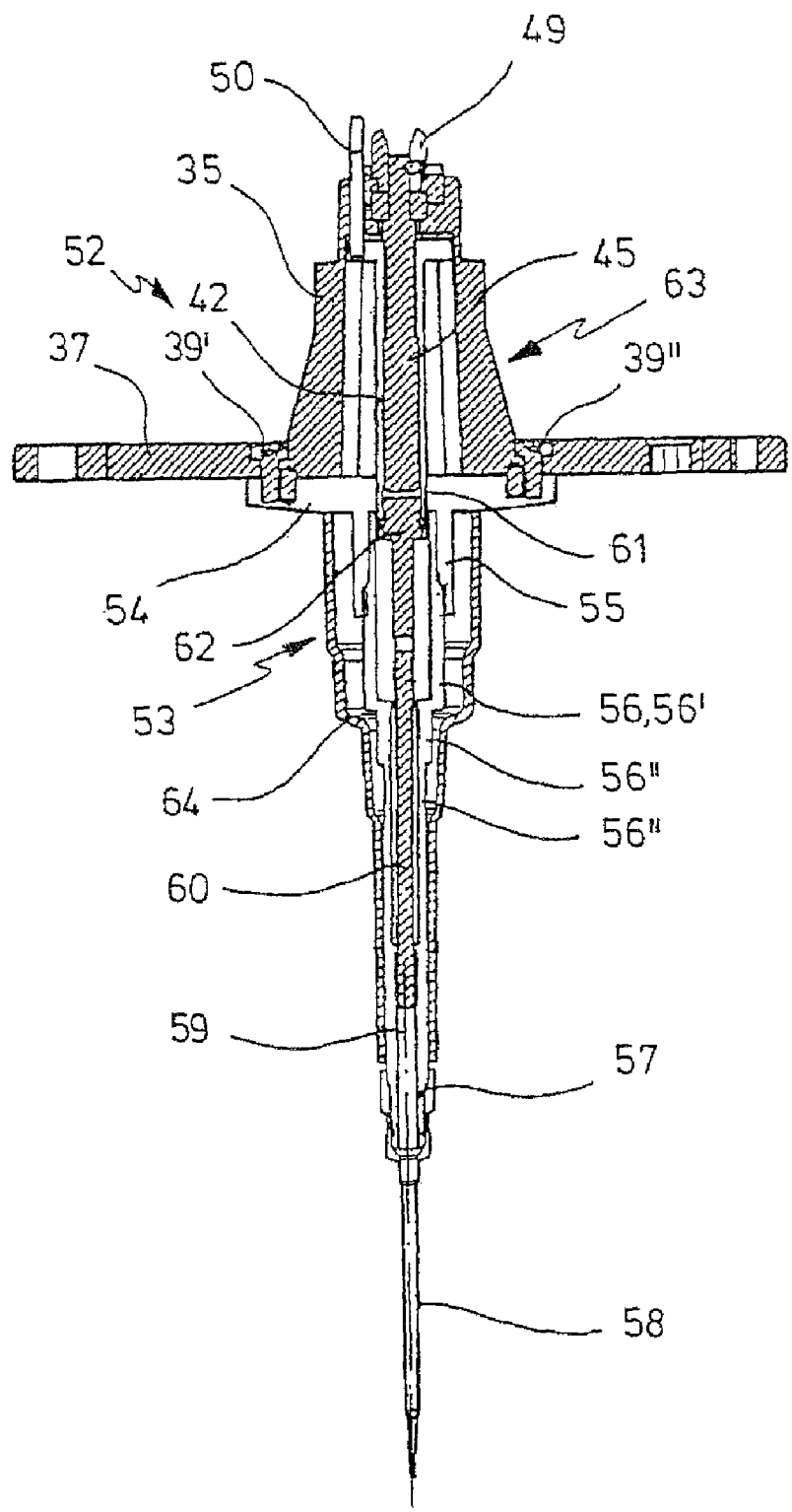
Figure 7:
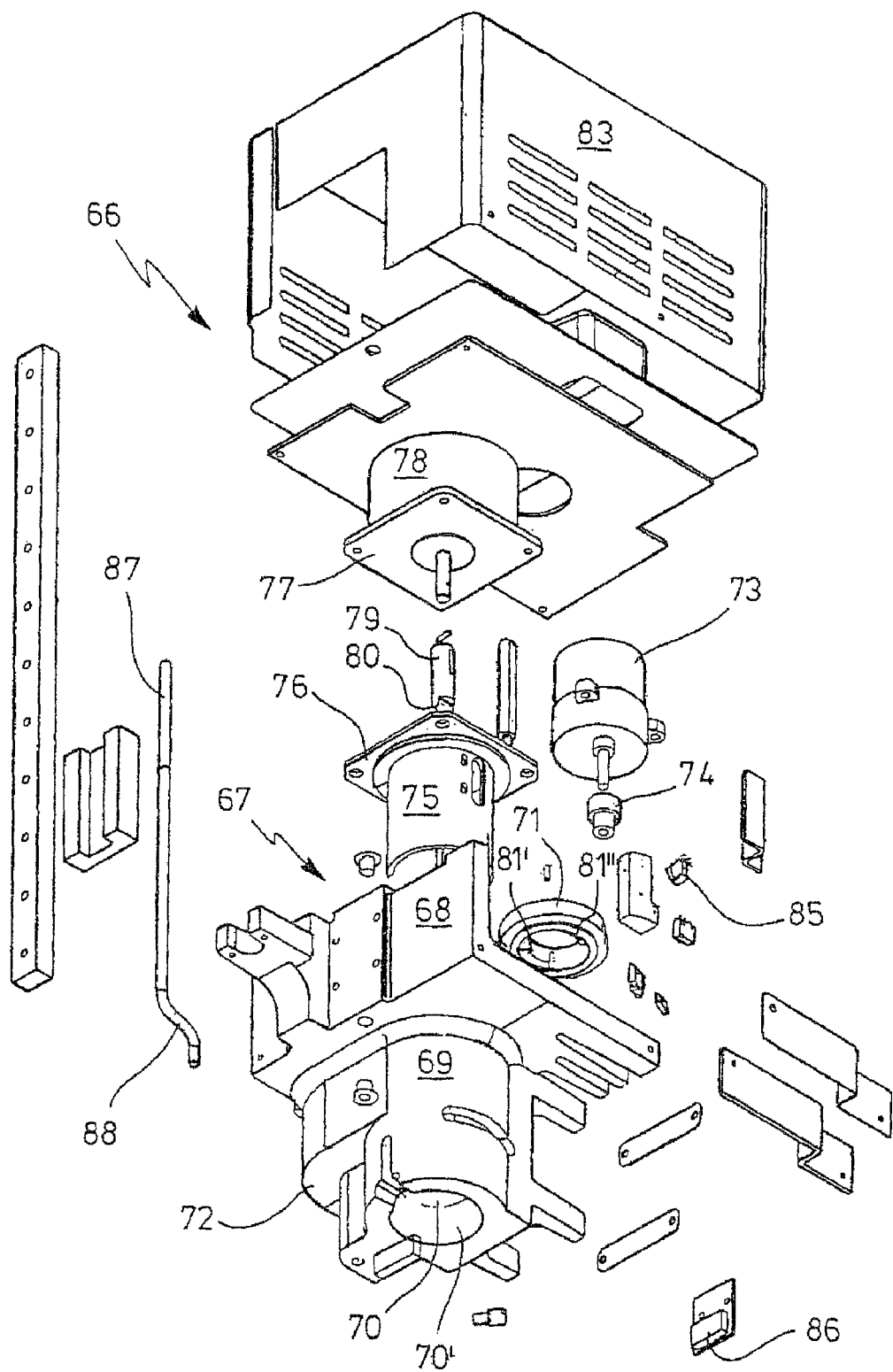
Figure 8:
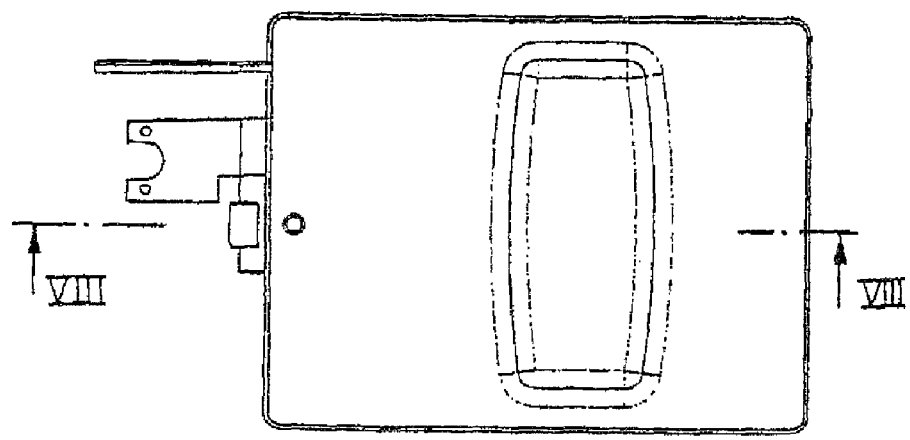
Figure 8:
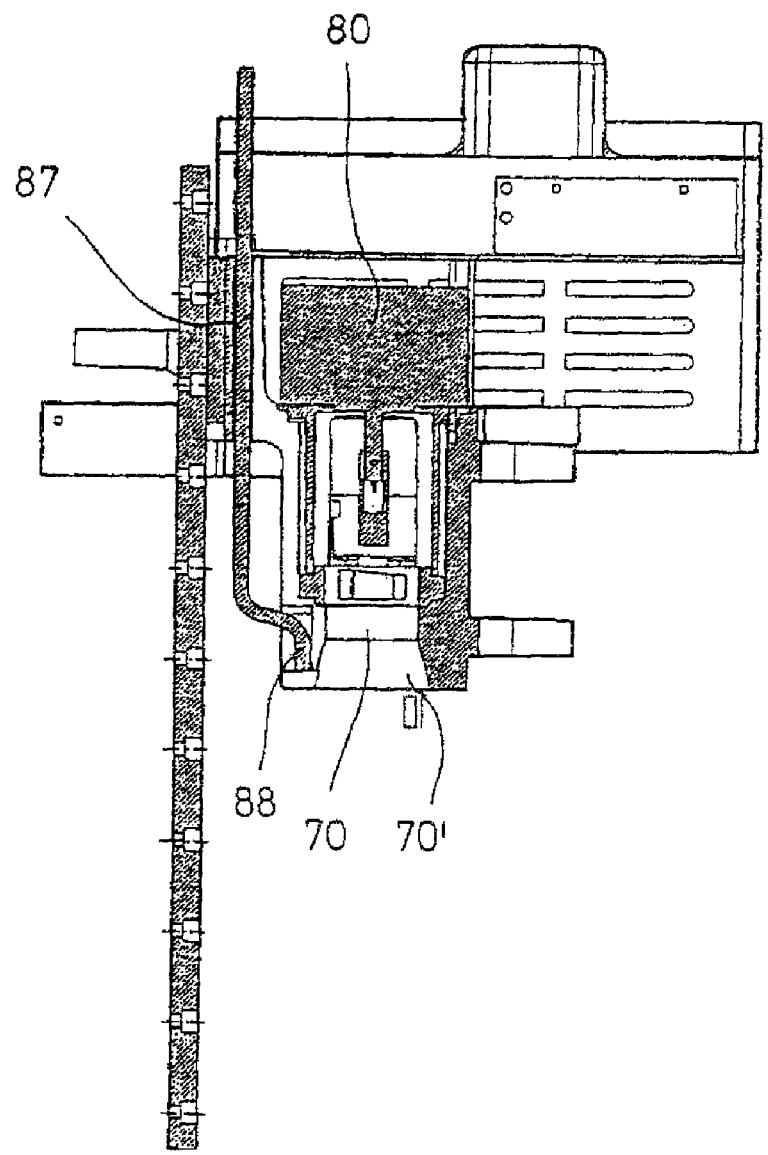
Figure 9:
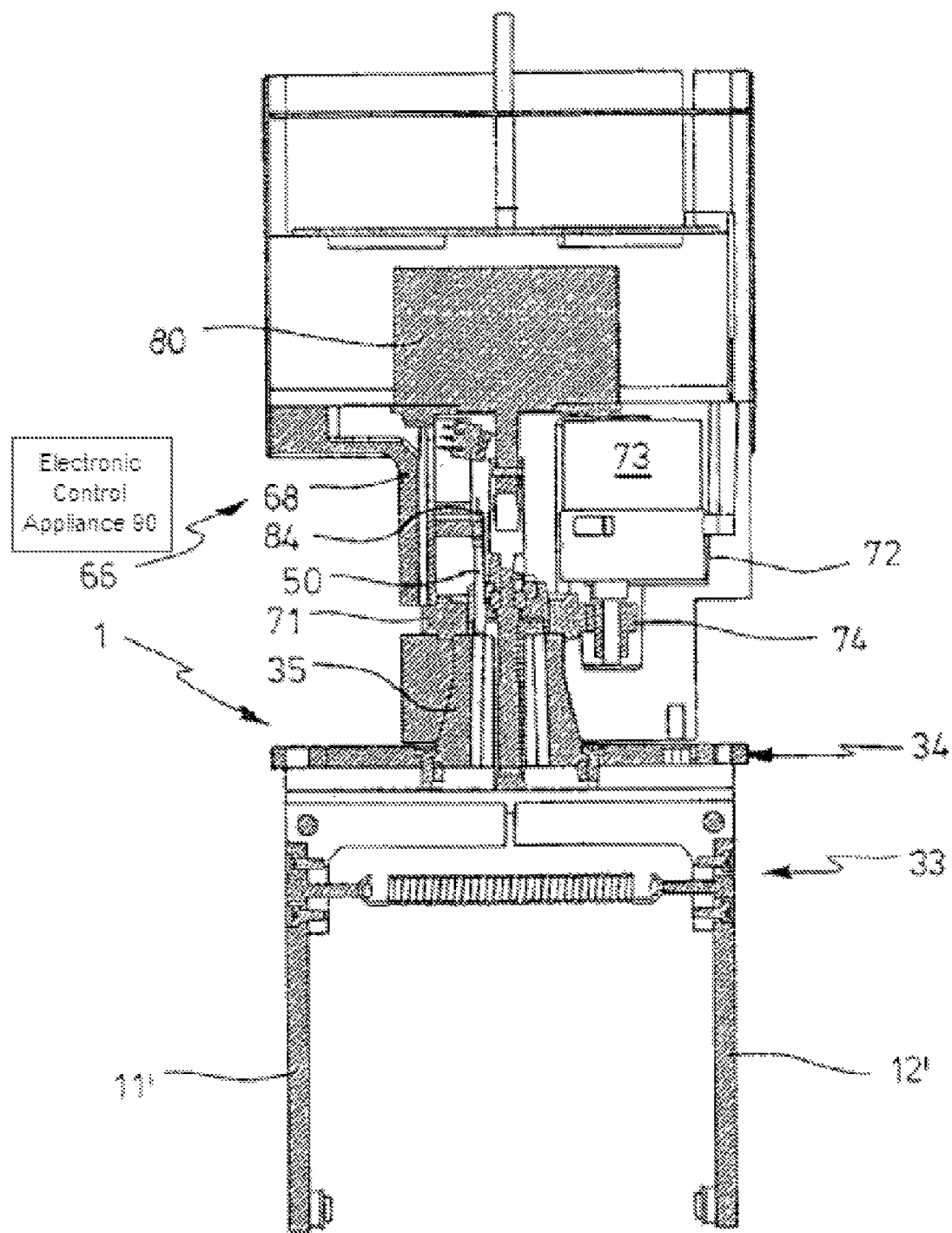
Figure 10:
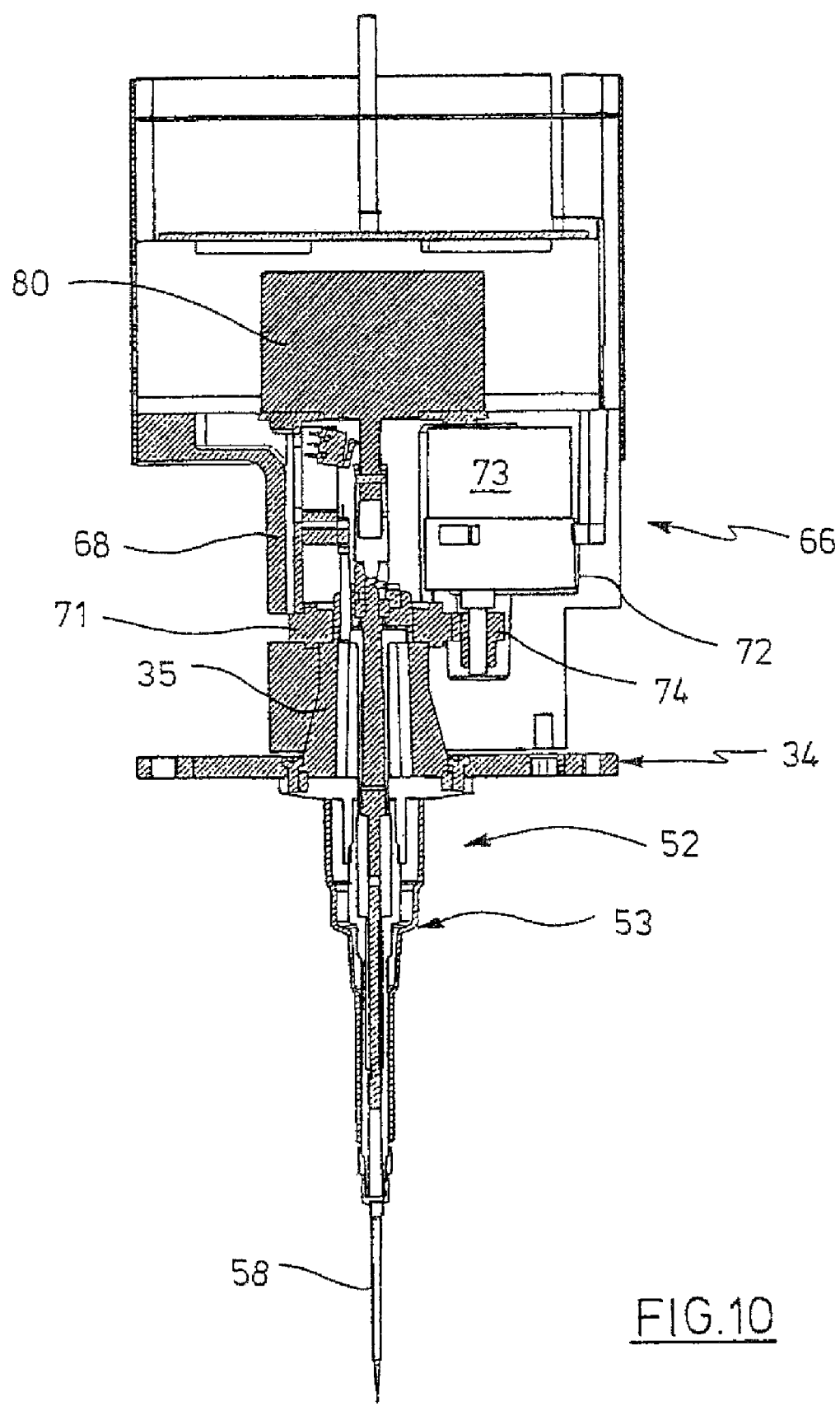

The invention is explained in more detail below, by means of the attached drawings of realization examples. In the drawings show:

FIG. 1 a gripping tool in an exploded perspective view;

FIG. 2 the same gripping tool, assembled, in a top view;

FIG. 3 the same gripping tool, assembled, in a vertical section;

FIG. 4 a dosage tool in a perspective view, transversal from the topside;

FIG. 5 the same dosage tool in a top view;

FIG. 6 the same dosage tool in a vertical section;

FIG. 7 a tool support for an automatic laboratory machine, in an exploded perspective view;

FIG. 8 the same tool support, assembled, in a vertical section;

FIG. 9 the same tool support, equipped with a gripping tool, in another vertical section;

FIG. 10 the same tool support, equipped with a dosage tool, in another vertical section;

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated According to FIG. 1 to 3, the gripping tool 1 has an essentially U-shaped bearing box 2, which has a groove 6 running transversally through the legs 3, 4 and into the basis 5. Through this, the legs 3,4 are subdivided into bearing blocks 3', 3", 4', 4". Through each leg 3,4 a bearing bore 7,8 runs in the longitudinal direction of the bearing box 2.

Further, the gripping tool 1 has two gripping levers 9, 10, which each have one grappler 11, 12 and a drive arm 13, 14 orthogonally offset to it.

On the short grapplers 11, 12 of the gripping levers 9, 10, T-shaped grappler extensions 11', 12' are detachably fixed on their middle legs 11", 12" by means of screws 13', 13", and 14', 14". On their transversal legs 11''', 12''', they have each a needle 15', 15", 16', 16" on both ends, projecting on the sides facing each other. These needles are each concentrically surrounded by a protecting sleeve 17', 17", 18', 18", each of which is supported via a helical spring 19', 19", 20', 20" on the transversal leg 11''', 12'''. The protective sleeves 17', 17", 18', 18" project up to the level of the points of the needles 15', 15", 16', 16" when they are not loaded, and are displaceable against spring action towards the transversal leg 11''', 12''' on the other hand.

In turn, liners 21', 21", 22', 22" are disposed concentrically around the protective sleeves 17', 17", 18', 18", which project less far than the needles 15', 15''', 16', 16''' from the transversal legs 11''', 12'''.

The gripping levers 9, 10 have transversally directed further bearing bores 23, 24 in the corners between the grapplers 11, 12 and the drive arms 13, 14. The gripping levers 9, 10 are inserted into the groove 6 and are mounted on bearing bolts 25 and 26, which are guided through the bearing bores 7, 23 and 8, 24. The bearing bolts 25, 26 are secured by locking rings 27', 27", 28', 28" on their ends.

Attachment bolts 29, 30 are inserted into the grapplers 11, 12, which are secured against pulling out on the sides farther from each other by a head, and which have transversal bores on the sides facing each other. Into these transversal bores, a helical extension spring 31 is hanged up with its end-sided ears.

The base body 2 has a transversally directed bore in its centre 32.

The above-mentioned elements form collectively a bottom part 33. On top of it, the gripping tool has an upper part 34. This has a hollow mounting spigot 35. The latter has an upper cylindrical portion 35', which has two claws 36', 36" on its outer perimeter, in order to form a bayonet-type lock. The claws 36', 36" have a faint thread pitch for twisting a bayonet-type connection.

Further, the spigot 35 has a middle cylinder part 35" with a larger diameter than the cylinder part 35', and a base part 35''' expanding itself conically downward.

The base part 35''' is fixedly connected on the bottom with a strip-shaped mounting plate 37. The mounting plate 37 is adjusted and fixed on the upper side of the base body 2 by means of pins 38', 38" and screws 39', 39". It is adjusted such that a bore 40, extending longitudinally through the mounting spigot 35 and transversally through the mounting plate 37, is aligned to the passage 32 of the base plate 2.

The bore 40 has two diametrically opposing longitudinal grooves 41', 41". A sleeve-shaped threaded nut 42 is inserted into the bore 40, which is guided in the longitudinal grooves 41', 41" with two wings 43', 43" radially projecting on the upside.

A plug-like separator 44 is inserted into the threaded nut 42 on the bottom.

Further, a spindle 45 is screwed into the threaded nut 42. This has a spigot portion 45" projecting from the threaded portion 45''', on which it is mounted in a ball bearing 46 which is screwed fast in the upper cylinder part 35' of the mounting spigot 35 by a bearing fixture 47.

On a portion of the spigot portion 45" projecting over the ball bearing 46, a driving feature 49 is fixed by a radial threaded pin 48 in a manner secured against rotation, which has a radially and axially oriented groove for insertion of a blade-shaped drive element on its free end.

In the wing 43" of the threaded nut 42, a cylinder pin 50 is fixed, which is guided through a groove 47' of the bearing fixture in a direction parallel to the central axis of the threaded nut 42, and which projects from the mounting spigot 35 on the upside.

On one side of the mounting plate 37, a printed circuit board 51 with a chip is fixed, in which data about the gripping tool 1 are stored. The chip can be read from the outside.

By turning the driving feature 49, the spindle 45, which is axially secured in the mounting spigot 35, moves axially the threaded nut 42, which on its part is unrotatably guided in the mounting spigot. When the threaded nut 42 is displaced towards the drive arms 13, 14, it pushes against their inner ends via the separator 44 and swings the grapplers 11, 12 apart, against the action of the spring 33. The gripping tool 1 is then positionable above an object which is to be seized. By turning the driving feature 49 in the opposite sense, the threaded nut 42 can be moved back, so that the extension spring 33 swings the grapplers 11, 12 together and their extensions 11''', 12''' swing against the vessel which is to seized. The grappler extensions 11', 12' are conceived for seizing a microtiter plate and push with the needles 15', 15", 16', 16" into its side walls or grasp with the liners 21', 21''', 22', 22" into lateral recesses of the microtiter plate.

The spring tension is sufficient to keep fast the microtiter plate. By means of the gripping tool 1 it is then transportable.

The grappler extensions 1', 12' are swingable apart by turning the drive feature 49, in order to release the microtiter plate. The grappler extensions 11', 12' can also be swung apart manually, in order to take out a microtiter plate. The respective position of the grapplers is indicated by the cylinder pin 50, the position of which is feelable from the outside by means of a sensor.

According to FIG. 4 to 6, a dosage tool 52 has a bottom part 53 with a base plate 54, from which a sleeve part 55 projects downward. A shaft 56 is screwed into the sleeve portion 55, which has a sequence of cylindrical portions 56', 56''' with diameters decreasing in the downward direction.

On the bottom end of the cylindrical section 56''', a cone 57 is formed, onto which a conventional pipette point 58 is pinned up.

The cylindrical portion 56''' contains a cylinder 59 in its bottom portion, into which a piston 60 is sealingly inserted. The piston 60 extends over and above the upper end of the shaft 56 up to a central bore 61 of the base plate 54. There, the piston 60 has an anchoring section 62.

An upper part 63 is fixed on the base plate 54, the construction of which corresponds accurately to that one of the upper part of the gripping tool 1. In being so, the threaded nut 42 is not equipped with a separator 44 on its bottom, but is screwed fast with the anchoring section 62 of the piston 60. As for the details, reference is made to the description of the upper part 34 above.

On the shaft 56 is guided a sleeve 64 for throwing off. The latter is pre-tensioned by a not shown spring facility towards the upper part 63. On its upper end, it has a laterally projecting actuation lug 65.

By turning the drive feature 49, the piston 60 is movable in the cylinder 59, in order to suck up sample liquid into the pipette point 58 or to eject it from it, respectively. In doing so, the respective position of the piston 60 is indicated by the cylinder pin 50. Upon movement of the actuation lug 65, the pipette point 58 can be pushed off from the cone 57 by means of the sleeve for throwing off 64.

According to FIGS. 7 and 8, the tool support has a base part 67, which has an essentially L-shaped section 68 and a an approximately sleeve-shaped section 69 projecting downward from it. The sleeve-shaped section 69 has a cylindrical accommodation 70, in which a bayonet-type locking ring 71 is rotatably mounted. The accommodation 70 has a conical initial section 70'. Beneath the sleeve-shaped section 69 there is a chamber 72, in which a drive motor 73 is disposed, which has a drive gearwheel 74 fixed on a shaft, which combs with the bayonet-type locking ring 71.

In the cylindrical accommodation 70 of the sleeve-shaped section 69, an eccentric ring 75 is guided, which has a flange 76 atop. On the flange 76, a servo motor 78 is screwed fast with a corresponding mating flange 77. On the shaft of the servo motor 78, a further coupling appliance 79 is fixed, the free end of which is provided with a blade 80.

The blade 80 is disposed somewhat above the bayonet-type locking ring 71. This is provided on its inner perimeter with claws 81''', 81''' diametrically opposing each other, which have a faint slope.

The base part 67 is closed by a box-like housing 83 on the upside. In the housing 83, above the base part 67, there are sensors 84 for the position recognition of a pin 50 which is axially inserted into the accommodation 70, and 84 for monitoring the position of the bayonet-type locking ring 71.

Externally to the housing, there is a sensor for the detection of a chip on the printed circuit board 51.

Further, a rod-shaped element 87 for throwing off is guided along on the outside of the base part 68, which is axially movable by means of a not shown linear drive. A hook-shaped end portion 88 of the element for throwing off 87 is associated to the conical opening region of the cylindrical accommodation 70.

According to FIG. 9, a gripping tool 1 is inserted in the cylindrical accommodation 70 (best seen in FIG. 7) of the tool support 66 with the mounting spigot 35, and fixed therein by turning the bayonet-type locking ring 71 by means of the drive motor 73. The sensor 84 detects the position of the cylinder pin 50, and by doing so the position of the grappler extensions 11', 12'. The auxiliary grapplers 11', 12' are swingable by controlling the servo motor 78 (best seen in FIG. 7). The tool support 66 is movable by means of a not shown XYZ drive appliance, in order to access different vessel positions of an automatic laboratory machine. An electronic control appliance 90 belonging to the tool support 66 controls the different motions.

Likewise, the gripping tool 1 is separable from the tool support 66, by moving to a deposition position and controlling the drive motor 73.

According to FIG. 10, a dosage tool 52 is correspondingly fixed on the tool support 66. The piston position is indicated by the cylinder pin 50. The data of the accommodated dosage tool 52 are communicated to the control appliance by reading out the chip on the printed circuit board 51. By actuating the servo motor 78, the driving feature 49 is turned by the coupling appliance 79, and the movement of the piston 60 is controlled. Through this is effected the take-up or release of sample liquid, respectively. The pipette point 58 is removable by (motor induced) moving the element for throwing off 87, which presses on the actuation lug 65. By actuating the drive motor 73, the dosage tool 52 is also readily connected to or separated from the tool support 66, respectively.

The above Examples and disclosure are intended to be illustrative and not exhaustive. These examples and description will suggest many variations and alternatives to one of ordinary skill in this art. All these alternative and variations are intended to be included within the scope of the attached claims. Those familiar with the art may recognize other equivalents to the specific embodiments described herein which equivalents are also intended to be encompassed by the claims attached hereto.

What is claimed is:

1. A combination comprising a tool support and a tool mounted to the tool support thereto:
    the tool support comprising a base which includes an L-shaped section and a sleeve-shaped section having a cylindrical accommodation; a bayonet-type locking ring rotatably mounted within the cylindrical accommodation; a drive appliance; a first coupling appliance; and a drive motor;
    the tool comprising: a second coupling appliance and a mounting appliance; wherein the tool is detachably mounted in the cylindrical accommodation with the mounting appliance; the mounting appliance being connected to the bayonet-type locking ring;
    wherein the first coupling appliance is rotatably and detachably connected to the second coupling appliance; and the drive appliance further comprises a servo motor connected to the first coupling appliance for driving the tool; and
    wherein the drive motor of the tool support further comprises a shaft and a drive gearwheel fixed on the shaft, said drive gearwheel combs with the bayonet-type locking ring when the bayonet-type locking ring rotates, and the drive motor rotates the bayonet-type locking ring to detachably mount the tool to the tool support, and
    a control appliance for controlling the movements of the tool and of the bayonet-type locking ring of the tool support.

2. The combination of claim 1, wherein the tool further comprises a pin and the tool support further comprises a first sensor for sensing the position of the pin and for monitoring the position of the bayonet-type locking ring, the first sensor being connected with the control appliance, in order to control the movement of the tool depending on the position of the pin.

3. The tool support combination of claim 1 wherein the tool is a gripping tool.

4. The tool support combination of claim 1 wherein the tool is a dosage tool.

* * * * *